(12) United States Patent  
Rueter et al.

(10) Patent No.: US 7,818,059 B2  
(45) Date of Patent: Oct. 19, 2010

(54) ATRIAL CAPTURE MANAGEMENT IN MINIMAL VENTRICULAR PACING SYSTEM AND METHOD

(75) Inventors: John C. Rueter, Woodbury, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 724 days.

(21) Appl. No.: 11/115,628

(22) Filed: Apr. 27, 2005

(65) Prior Publication Data

US 2006/0247705 A1 Nov. 2, 2006

(51) Int. Cl.  
*A61N 1/362* (2006.01)

(52) U.S. Cl. .................. 607/28; 607/9; 607/27

(58) Field of Classification Search .......... 607/9, 607/28  
See application file for complete search history.

(56) References Cited

U.S. PATENT DOCUMENTS

| | | | |
|---|---|---|---|
| 5,052,388 A | 10/1991 | Sivula et al. | 128/419 PG |
| 5,320,643 A | 6/1994 | Roline et al. | 607/28 |
| 5,345,362 A | 9/1994 | Winkler | 361/681 |
| 5,601,615 A | 2/1997 | Markowitz et al. | 607/28 |
| 5,782,889 A | 7/1998 | Hognelid et al. | 607/28 |
| 5,954,755 A * | 9/1999 | Casavant | 607/28 |
| 6,389,316 B1 | 5/2002 | Bornzin et al. | 607/28 |
| 6,772,005 B2 | 8/2004 | Casavant et al. | 607/4 |
| 7,280,868 B2 * | 10/2007 | Rueter et al. | 607/9 |
| 2002/0183798 A1 | 12/2002 | Vonk | |
| 2003/0078627 A1 | 4/2003 | Casavant et al. | 607/9 |
| 2003/0083700 A1 | 5/2003 | Hill | 607/9 |
| 2003/0083712 A1* | 5/2003 | Rueter et al. | 607/28 |
| 2003/0195579 A1 | 10/2003 | Bradley et al. | 607/27 |
| 2003/0204214 A1 | 10/2003 | Ferek-Petric | 607/27 |
| 2004/0030358 A1 | 2/2004 | Rueter et al. | |
| 2004/0088019 A1 | 5/2004 | Rueter et al. | |
| 2004/0260352 A1 | 12/2004 | Rueter et al. | 607/28 |
| 2005/0021095 A1 | 1/2005 | Rueter et al. | 607/9 |

FOREIGN PATENT DOCUMENTS

EP 1116495 7/2001

* cited by examiner

*Primary Examiner*—Carl H Layno  
*Assistant Examiner*—Joseph Stoklosa  
(74) *Attorney, Agent, or Firm*—Stephen W. Bauer

(57) ABSTRACT

Embodiments of the invention provide systems and methods for an implantable medical device comprising means for selecting between an atrial chamber reset (ACR) test and an atrioventricular conduction (AVC) test to provide atrial capture management and means for switching between an atrial-based pacing mode and a dual chamber pacing mode based on detecting relatively reliable atrioventricular conduction.

18 Claims, 16 Drawing Sheets

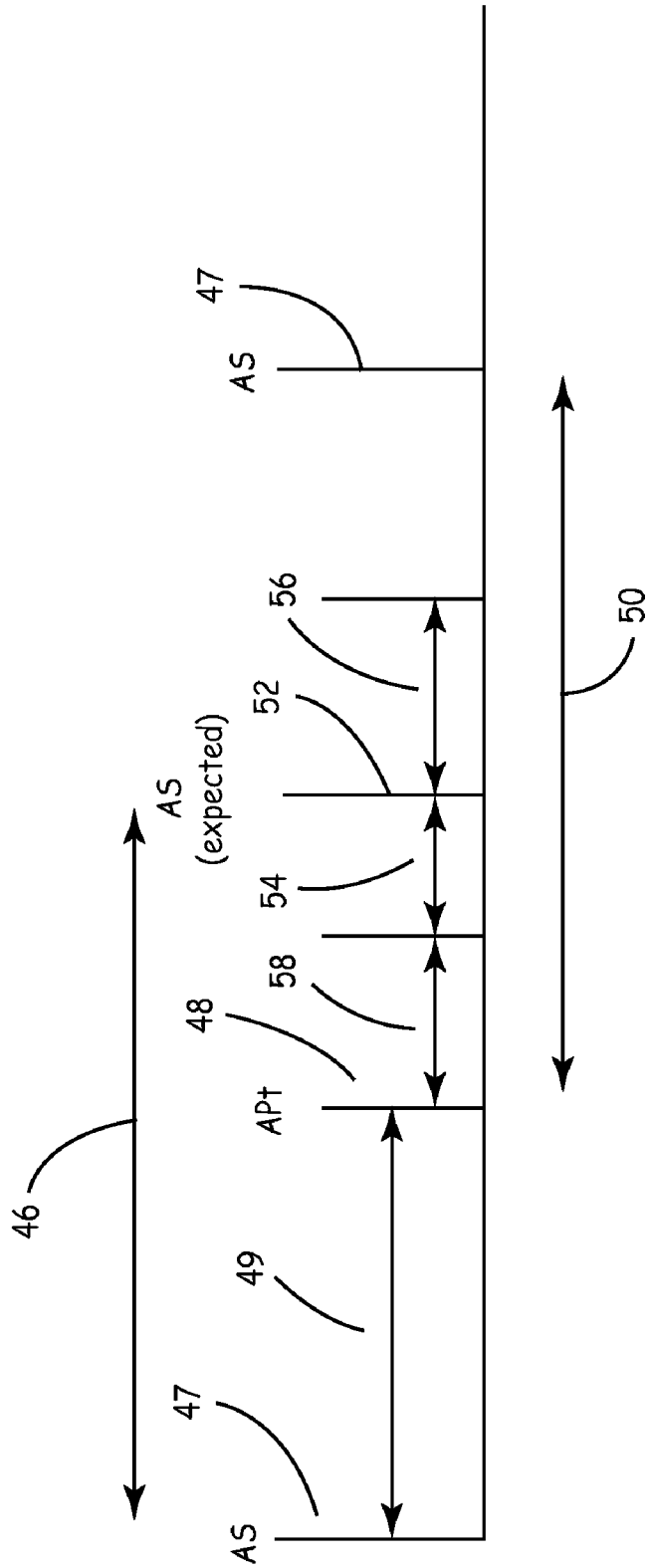

ATRIAL CAPTURE MANAGEMENT IN MINIMAL VENTRICULAR PACING SYSTEM AND METHOD

FIELD SECTION

The disclosure relates to a system and method for cardiac rhythm management for implantable medical devices such as pacemakers.

BACKGROUND SECTION

As described in commonly assigned U.S. Pat. No. 5,320,643, incorporated herein by reference, a cardiac pacemaker is an electrical device implemented to rectify an abnormal heart's natural pacing function by delivering appropriately timed electrical stimulation signals designed to cause the myocardium of the heart to depolarize. Many traditional devices unnecessarily pace in the ventricle. Inappropriate ventricular pacing may have short-term hemodynamic effects and may not be desirable when allowed to continue for an extended period of time. Several devices designed to reduce unnecessary pacing in the ventricle have been developed. An example of such a device is described in commonly assigned U.S. Patent Application Publication No. 2003/0078627, the contents of which are hereby incorporated by reference.

Further, the amplitude and pulse width of the pacing pulses must be of such a magnitude above the stimulation threshold to maintain capture so as to prevent serious complications. Yet, it is desirable that these pacing output parameters are no higher than a reasonable safety margin above the stimulation threshold in order to prolong battery life. The patient's stimulation thresholds in the atrium and ventricle often fluctuate in the short term, and gradually change over the long term. Some devices have been developed to provide atrial capture management (ACM) in traditional dual chamber pacing devices. An example of such a device is described in commonly assigned U.S. Patent Application Publication No. 2004/0030358, incorporated herein by reference.

BRIEF SUMMARY SECTION

Certain embodiments of the invention provide an implantable medical device comprising means for selecting between an atrial chamber reset (ACR) test and an atrioventricular conduction (AVC) test to provide atrial capture management (ACM), and means for switching between an atrial-based pacing mode and a dual chamber pacing mode based on detecting relatively reliable atrioventricular conduction to provide minimal ventricular pacing (MVP).

Certain embodiments of the invention include a software system implemented in a medical device system comprising means for selecting between an ACR test and an AVC test to provide atrial capture management, means for implementing an atrial-based pacing mode, means for detecting relatively reliable atrioventricular conduction, means for automatically switching to a dual chamber mode in the absence of relatively reliable AV conduction, means for resuming the atrial-based pacing mode upon detection of relatively reliable atrioventricular conduction, and means for biasing in favor of the ACR test when the medical device is in the dual chamber pacing mode.

Certain embodiments of the invention include a method of providing capture management to an implantable medical device biased towards an atrial-based pacing mode, comprising the steps of pacing an atrial chamber of a heart pursuant to the atrial-based pacing mode, detecting an intrinsic ventricular depolarization, determining whether a relatively reliable atrioventricular conduction condition exists, and if the conduction condition is present continuing the atrial-based pacing mode, and if the conduction condition is not present mode switching to a dual chamber pacing mode, and selecting between an atrial chamber reset (ACR) test and an atrioventricular conduction (AVC) test to provide atrial capture management, wherein the ACR test is selected when the medical device is in the dual chamber pacing mode.

BRIEF DESCRIPTION OF THE DRAWINGS

FIG. 10 is a timing diagram that typifies the various intervals corresponding to FIG. 9.

DETAILED DESCRIPTION OF THE ILLUSTRATED EMBODIMENTS

Figure 1:
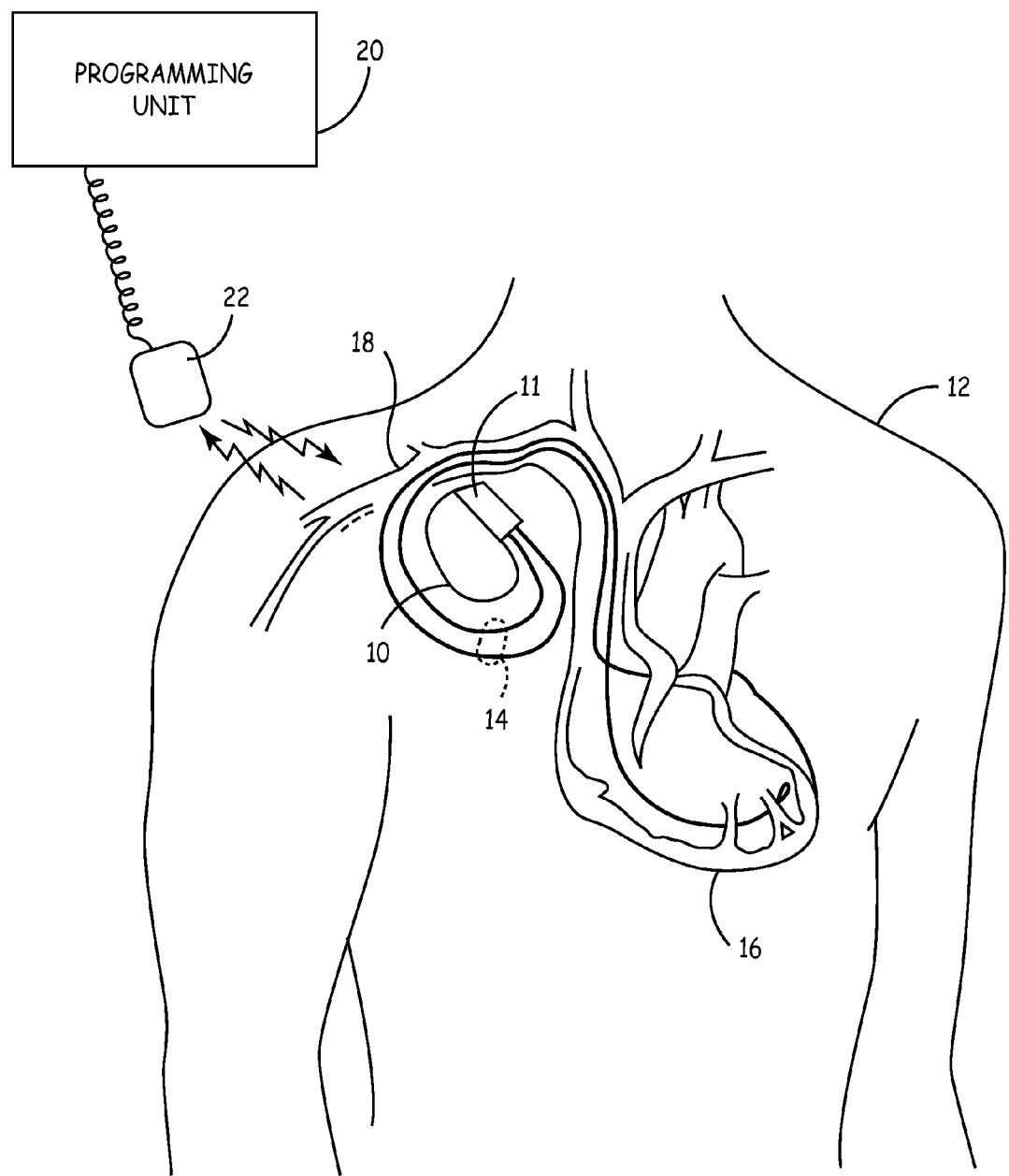
FIG. 1 is an illustration of a body-implantable device system in accordance with an embodiment of the invention.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention.

FIG. 1 is an illustration of an implantable medical device system adapted for use in accordance with the present invention. The medical device system shown in FIG. 1 includes an implantable device 10 (e.g., a pacemaker) that has been implanted in a patient 12. Device 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to device 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. Leads 14 may be implanted with its distal end situated in the atrium and/or ventricle of heart 16.

Although the invention will be described herein in one embodiment which includes a pacemaker, those of ordinary skill in the art will appreciate that the invention may be advantageously practiced in connection with numerous other types of implantable medical device systems, and indeed in any application in which it is desirable to provide the preferred atrial based pacing mode along with dual chamber pacing capabilities as may occur in implantable cardioverter defibrillators (ICDs) and the like. Further, the invention may be advantageously practiced in a device providing bi-ventricular pacing (bi-V) modes. Bi-V cardiac pacing systems for improving cardiac function for heart failure patients that pace and sense in the right and left ventricles of the heart are described in U.S. Patent Application Publication No. US 2003/0083700, the contents of which are hereby incorporated by reference.

Also depicted in FIG. 1 is an external programming unit 20 for non-invasive communication with implanted device 10 via uplink and downlink communication channels. Associated with programming unit 20 is a programming head 22, in accordance with conventional medical device programming systems, for facilitating two-way communication between implanted device 10 and programmer 20. An example of a programmer 20 is described in U.S. Pat. No. 5,345,362, which is hereby incorporated by reference.

Figure 2:
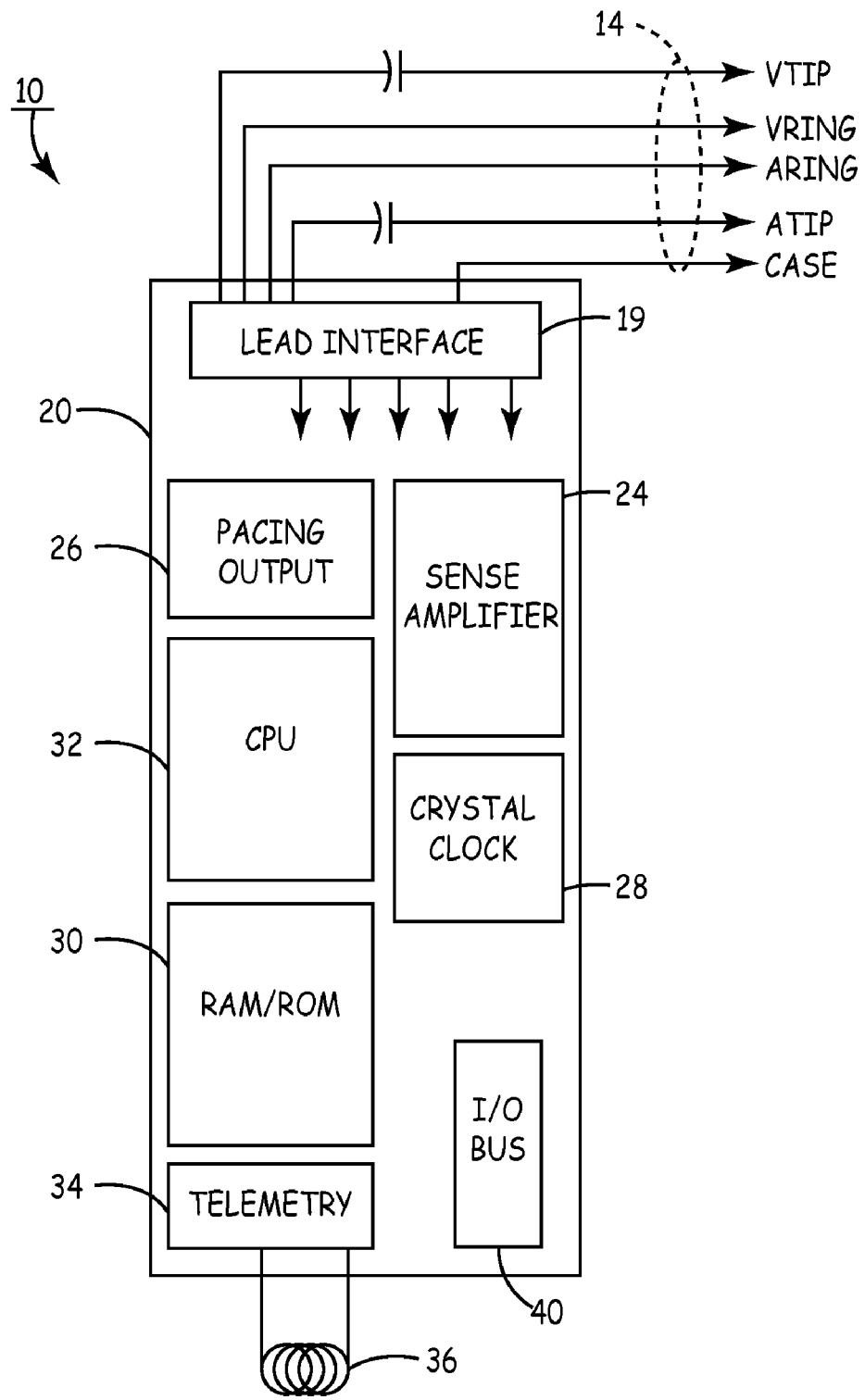
FIG. 2 is a block diagram of an implantable medical device in accordance with an embodiment of the invention.

FIG. 2 is a block diagram of an embodiment of some of the electronic circuitry that makes up device 10. As can be seen from FIG. 2, device 10 comprises a primary stimulation control circuit 20 for controlling the device's pacing and sensing functions. The circuitry associated with stimulation control circuit 20 may be of conventional design, in accordance, for example, with what is disclosed U.S. Pat. No. 5,052,388, the contents of which is hereby incorporated by reference. Stimulation control circuit 20 may include sense amplifier circuitry 24, stimulating pulse output circuitry 26, a crystal clock 28, a random-access memory and read-only memory (RAM/ROM) unit 30, and a central processing unit (CPU) 32, all of which are well-known in the art. Device 10 may also include an internal communication circuit 34 so that it is capable communicating with external programmer/control unit 20.

With continued reference to FIG. 2, device 10 is coupled to one or more leads 14 which, when implanted, extend transvenously between the implant site of device 10 and the patient's heart 16, as previously noted with reference to FIG. 1. Physically, the connections between leads 14 and the various internal components of device 10 are facilitated by means of a conventional connector block assembly 11, shown in FIG. 1. Electrically, the coupling of the conductors of leads and internal electrical components of device 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of device 10. For the sake of clarity, the specific connections between leads 14 and the various components of device 10 are not shown in FIG. 2, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or micro controller, but in the present invention is a custom integrated circuit. Although specific connections between CPU 32 and other components of stimulation control circuit 20 are not shown in FIG. 2, CPU 32 may function to control the timed operation of stimulating pulse output circuit 26 and sense amplifier circuit 24 under control of programming stored in RAM/ROM unit 30.

With continued reference to FIG. 2, crystal oscillator circuit 28 is, for example, a 32,768-Hz crystal controlled oscillator that provides main timing clock signals to stimulation control circuit 20. Again, the lines over which such clocking signals are provided to the various timed components of device 10 (e.g., microprocessor 32) are omitted from FIG. 2 for the sake of clarity. Further, it is to be understood that the various components of device 10 depicted in FIG. 2 are powered by means of a battery (not shown) that is contained within the hermetic enclosure of device 10.

Stimulating pulse output circuit 26, which functions to generate cardiac stimuli under control of signals issued by CPU 32, may be of any suitable type. Again, it is believed that those of ordinary skill in the art could select from among many various types of prior art pacing output circuits that would be suitable for the purposes of practicing the present invention.

Sense amplifier circuit 24, which may be of conventional design, functions to receive electrical cardiac signals from leads 14 and to process such signals to derive event signals reflecting the occurrence of specific cardiac electrical events, including atrial contractions (P-waves) and ventricular contractions (R-waves). Sensed amplifier 24 provides these event-indicating signals to CPU 32 for use in controlling the synchronous stimulating operations of device 10. In addition, these event-indicating signals may be communicated, via uplink transmission, to external programming unit 20 for visual display to a physician or clinician. Those of ordinary skill in the art will appreciate that device 10 may include numerous other components and subsystems, for example, activity sensors and associated circuitry.

Figure 3:
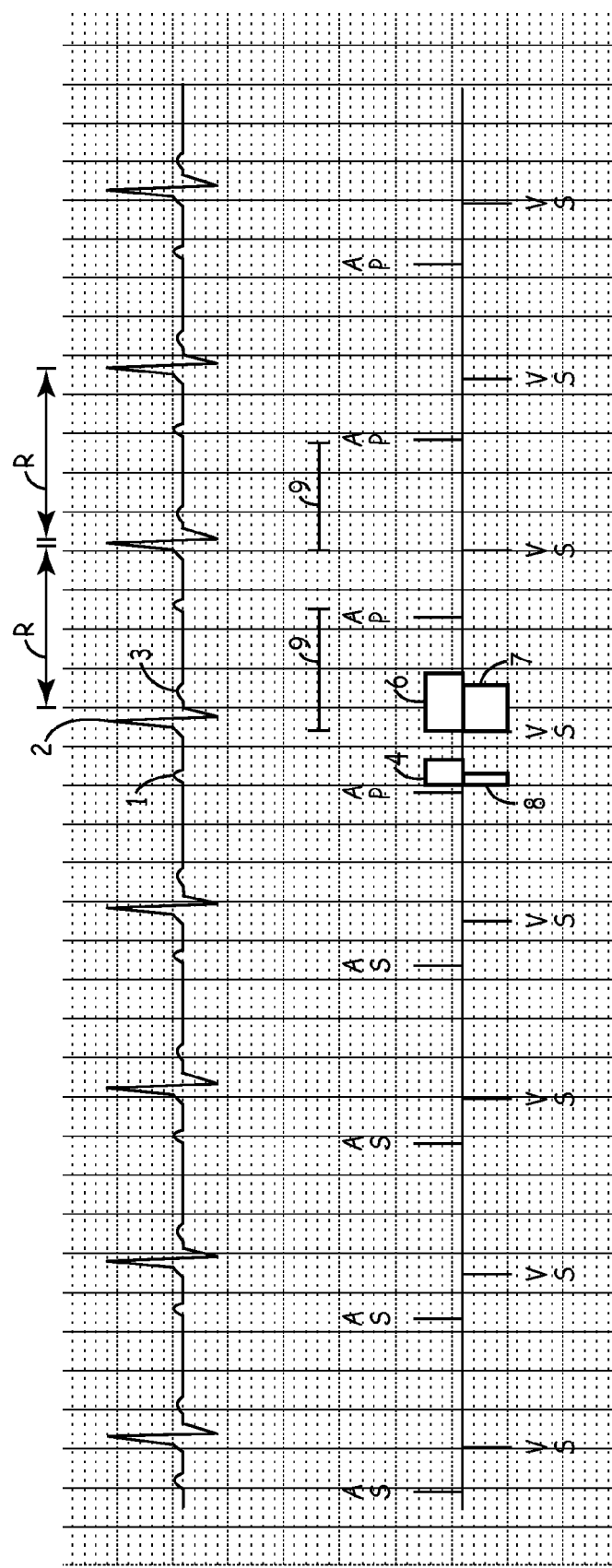
FIG. 3 is a ladder diagram of an ADI/R operation in accordance with an embodiment of the invention.

Device 10 may be adapted to provide an atrial based pacing mode. Examples of suitable atrial based pacing modes include ADI/R and AAI/R modes. In some embodiments, device 10 is biased to operate in the atrial based pacing mode to limit unnecessary ventricular pacing. FIG. 3 is a ladder diagram of an AAI/R operation. Per the NBG Code, the letter in the first position (A) means that the pacemaker (or other implanted device) will pace the atrium in the absence of an atrial sensed event. The second letter (D) implies that the pacemaker will sense in dual chambers, that is, both the atrial and ventricular chambers. The third letter (I) means that, upon sensing in either chamber, pacing will be inhibited in that specific chamber. The final letter, R, implies that the device may be rate responsive, that is, altering the atrial rate in response to an artificial sensor, such as a Piezo-electrical crystal, accelerometer, minute ventilation, etc.

The operation of the AAI/R mode is depicted in the ladder diagram as follows. Atrial paced (or sensed) event 1 initiates a blanking period 4, followed by auto-adjusting atrial sensitivity (not shown). Sensing circuitry (see FIG. 2) determines if and when ventricular sensed event 2 has occurred. If detected, timing circuitry (see FIG. 2) initiates VA interval 9. Other timing, blanking periods, and refractory periods serve the following purposes. A programmable ventricular blanking period 8 prevents sensing of atrial pace 1 on the ventricular channel, sometimes termed "crosstalk." Ventricular sensed event 2 starts a post ventricular atrial blanking (PVAB) period 6 (e.g., 120 ms), followed by auto-adjusting atrial sensitivity. PVAB 6 serves the purpose of preventing sensing of the R-wave or T-wave on the atrial channel, termed "far-field R-wave sensing." Ventricular sensed event 2 also starts a ventricular blanking 7 (e.g., 100 ms) followed by auto-adjusting ventricular sensitivity. This period serves the purpose of preventing sensing of the ventricular output pulse or the ventricular depolarization itself. Repolarization, or T-wave 3, follows R-wave 2. Ventricular event 2 detected by sensing circuitry (see FIG. 2) sends signal to timing circuitry to start VA interval 9, leading to the next atrial pacing cycle. Several R-R intervals are depicted in FIG. 3.

Figure 4:
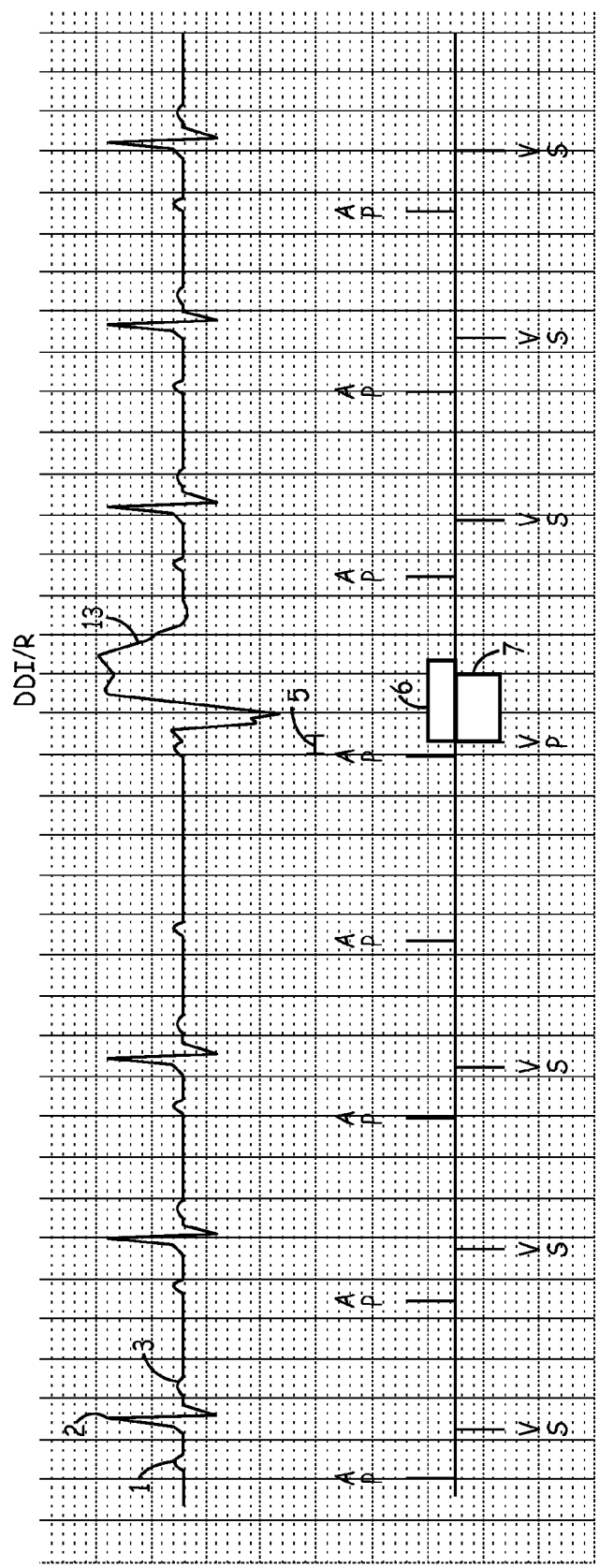
FIG. 4 is a ladder diagram of a backup ventricular pace during an episode of transient AV block in accordance with an embodiment of the invention.

The atrial based pacing mode may generally be used primarily with sick sinus patients who have full or some degree of intact AV conduction. In the presence of relatively reliable intact AV conduction the pacemaker will maintain the atrial based (e.g., ADI/R) operation/mode. Sensed ventricular events would occur in the vast majority of cardiac cycles (that is, PQRST). FIG. 4 teaches what will occur should the patient develop transient AV block for one or a few cardiac cycles.

In the event that AV conduction becomes unreliable, device 10 is adapted to switch to a dual chamber pacing mode. Examples of dual chamber pacing modes include DDD/R and DDI/R pacing modes. FIG. 4 is a ladder diagram of the ventricular backup operation in the event the patient experiences a transient loss of AV conduction. The purpose of the ventricular backup operation is to maintain ventricular support (i.e., ensure that the ventricle is paced so the interval between ventricular contractions is limited to only one cycle). Briefly stated, in some embodiments the implanted device mode switches from the atrial based pacing mode to the dual chamber based pacing mode in response to a transient loss of AV conduction for at least one cardiac cycle.

The timing of the DDI/R may be as follows. In the DDI/R mode (fourth pacing cycle, labeled DDI/R), AV interval 5 is set to a short period (e.g., 80 ms), following the paced P-wave due to the presence of a PVC between the second and third atrial paced events. The purpose of this short AV interval 5 is intended to suppress competition between ventricular pacing pulse culminating in paced R-wave 13 and any potential intrinsic R-wave with a delayed conduction from the previous paced atrial event. Assuming the presence of such an intrinsic R-wave, the timing of the ventricular output pulse would normally result in a ventricular pacing pulse falling into the absolute refractory period of the intrinsic, conducted R-wave, resulting in a psuedo-fusion beat (not shown). This operation is intended to prevent the onset of a ventricular tachycardia, should the ventricular pacing pulse fall into the relative refractory period of the ventricle, commonly called "pacing on T" phenomenon.

With respect to the foregoing, in some embodiments of the invention, if the A-Pace (Ap) encroaches on the preceding V-Sense (Vs) (e.g. within 300 ms) for more than about four depolarization events (e.g., consecutive beats), then the pacing rate is decreased. In effect, this creates a dynamic upper sensor rate. To counter potential disadvantageous patient symptoms that may arise from the relatively short Vs-Ap intervals, the MVP modality can operate such that after a Vs event, a scheduled Ap event is delayed until some pre-defined interval expires. This aspect of the MVP modality is somewhat similar to upper tracking rate (UTR) hold-off or non-competitive atrial pacing (NCAP) hold-off except that it is based on an Ap event following a Vs. This results in the atrium being paced at a slightly lower rate than intended which may create issues that are known to exist with respect to so-called atrial overdrive pacing algorithms. In some embodiments, this aspect of the MVP modality is implemented in hardware primarily because of the critical timing involved.

Continuing with the timing in FIG. 4, paced R-wave 13 starts a ventricular blanking period 7, followed by auto adjusting ventricular sensitivity (not shown). Paced R-wave 13 also starts a PVAB 6 followed by auto adjusting atrial sensitivity (not shown). Assuming the transient AV block self-corrects and a sensed R-wave is detected in response to the ventricular pace (Vp), the atrial based pacing mode resumes with the next paced or sensed P-wave, as is depicted in FIG. 3.

Figure 5:
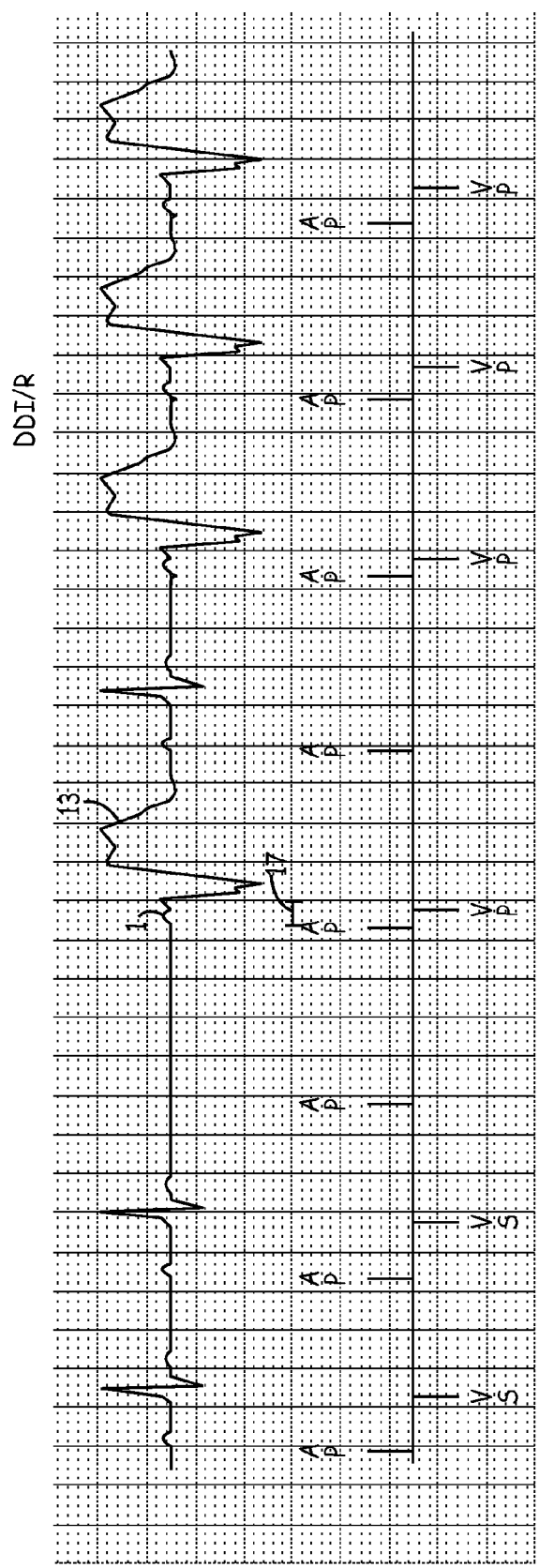
FIG. 5 is a ladder diagram depicting the pacing operation in the event that the patient develops AV block in accordance with an embodiment of the invention.

FIG. 5 is a ladder diagram that depicts the pacing operation in the event that the patient develops AV block for more than one cycle. Following a mode switch to DDD/R, VA interval 9 times out, resulting in atrial paced event 1. A very long (e.g. 400 ms or up to approximately 70% of the median V-V interval, or longer) 17 may be used in an attempt to promote native AV conduction (or a Vp stimulus may be withheld) as further described herein below. If, however, AV interval 17 is not interrupted by a sensed, intrinsic R-wave, as is depicted in the first cycle (labeled ADI/R), the pacemaker may immediately switch to the DDD/R mode. In the event that a sensed, intrinsic R-wave does occur, the device reverts to the atrial based pacing mode operation. The DDD/R operation, with the programmed AV interval, will be sustained until a sensed, intrinsic R-wave is detected, as further described herein. Mode switching to DDIR may occur in the event that an atrial tachycardia is detected.

Figure 6:
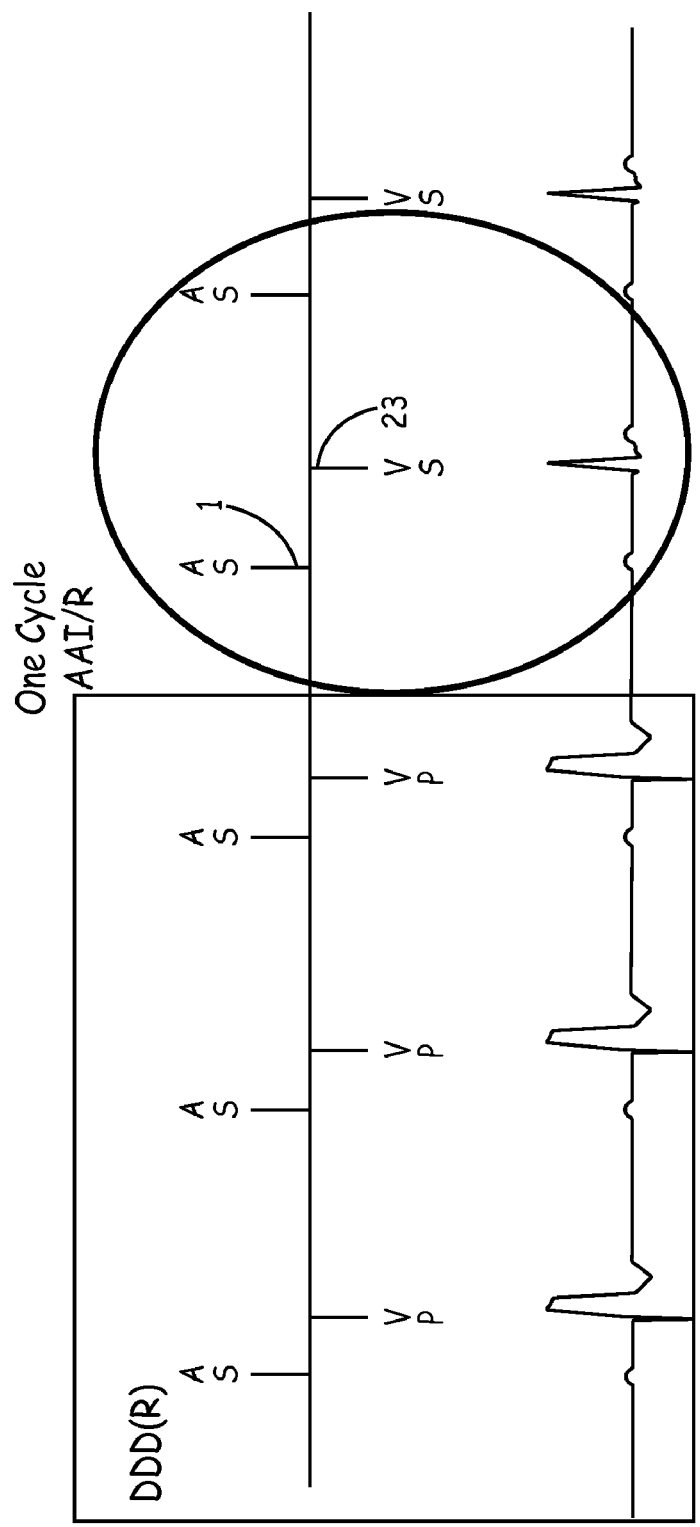
FIG. 6 is a diagram that depicts a periodic attempt to restore the ADI/R operation during sustained DDD/R operation where AV conduction occurs in accordance with an embodiment of the invention.
Figure 6A:
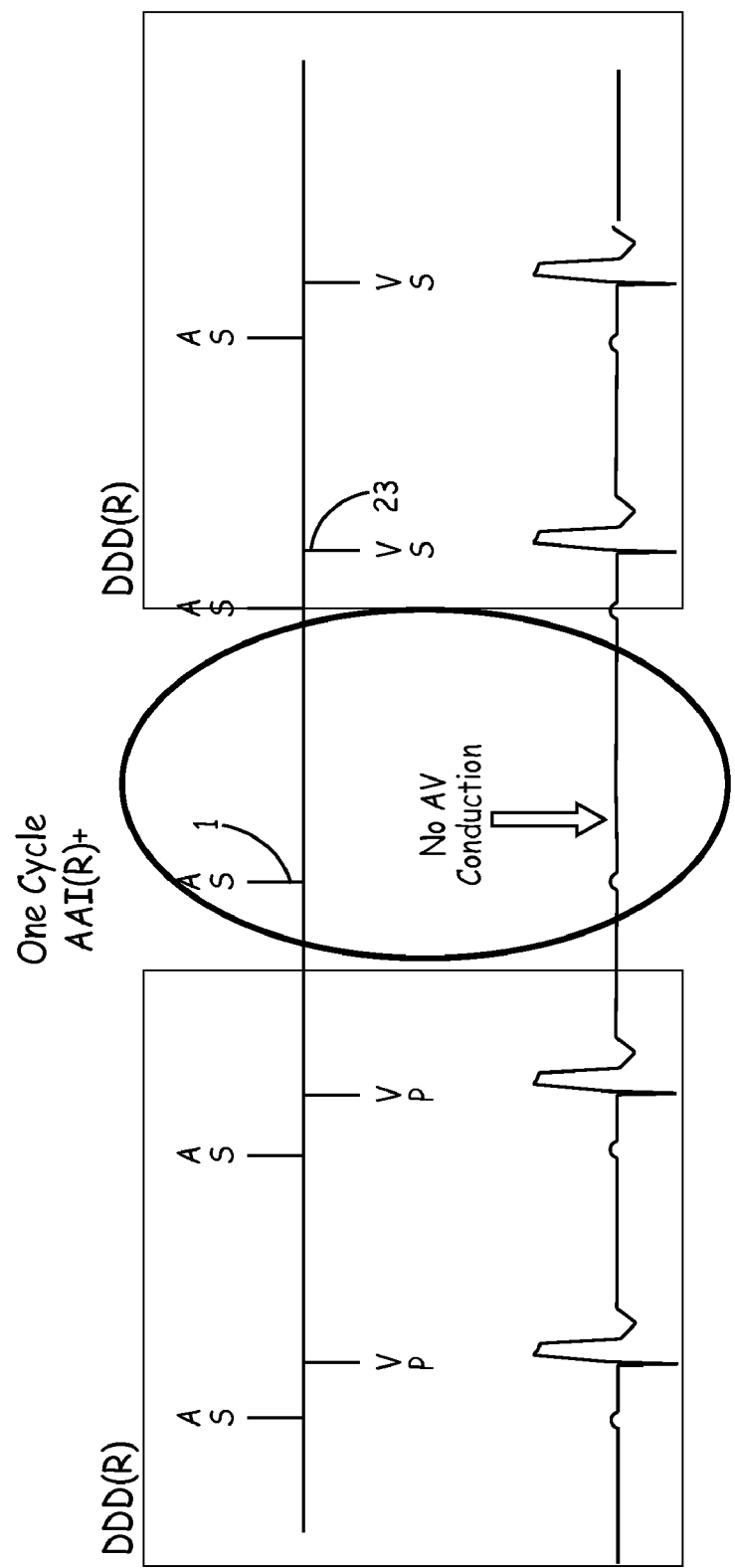
FIG. 6A is a diagram that depicts a periodic attempt to restore the ADI/R operation during sustained DDD/R operation where no AV conduction occurs in accordance with an embodiment of the invention.

Some embodiments of the invention are biased to pace in the atrial based pacing mode. FIG. 6 is a diagram that depicts a periodic attempt to restore the atrial based pacing mode (e.g., AAI/R) operation during sustained dual chamber pacing operation. As mentioned, the DDD/R mode may become the sustained mode of operation in the event that the patient develops a prolonged AV block, such as might occur with rate-dependent AV block or if the AV conduction become relatively unreliable. In such cases, the device may be programmed to revert to AAI/R 1 after a programmable number of DDD/R cycles. Then, the device looks for a ventricular sensed event, e.g., at 23 following atrial pace 1. In the event that a sensed, intrinsic R-wave is detected, the AAI/R operation is immediately resumed. In the absence of a ventricular sensed event, the device continues to operate in the DDD/R mode, as indicated in FIG. 6A.

Figure 7:
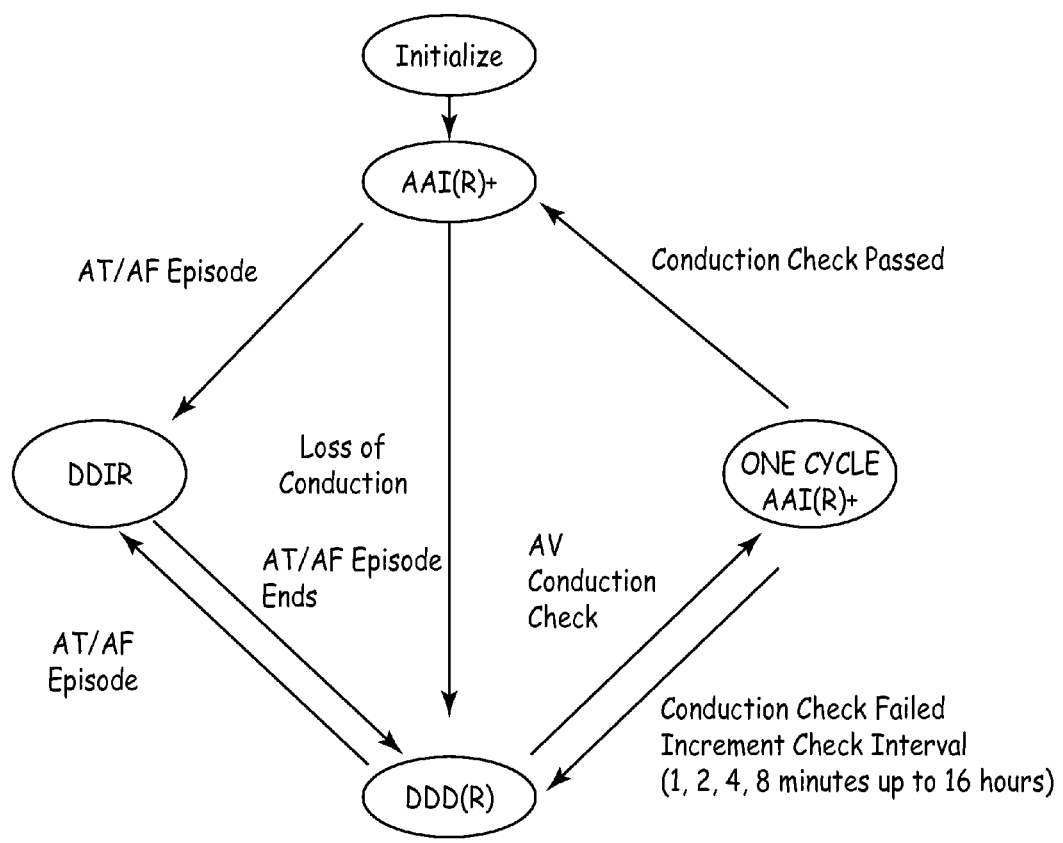
FIG. 7 is a diagram of a mode supervisor in the event that the patient develops an atrial tachycardia in accordance with an embodiment of the invention.

FIG. 7 is a diagram of a mode supervisor in the event that the patient develops an atrial tachycardia (AT) or atrial fibrillation (AF). A sick sinus patient often has episodes of AT, atrial flutter, or atrial fibrillation. During these episodes, the pacing operation must be set such that the ventricular pacing rate will neither be synchronized to the fast atrial rate nor so slow as to cause symptoms. Preferably during episodes of AT, the atrial-based pacing ends and a non-tracking (i.e. DDIR) pacing mode with rate response enabled is employed to provide ventricular pacing support.

In FIG. 4 it was noted that the device, while operating in the atrial based pacing mode, can switch to the DDI/R mode in response to transient loss of capture. The DDI/R mode also is well suited for pacing in the presence of an atrial tachycardia because it will not allow ventricular synchronization to a fast atrial rate nor will it allow the ventricular pacing rate to go below the programmed lower rate. Therefore, when an atrial tachycardia does occur, fast atrial sensed events without a conducted ventricular event have no effect on ventricular timing. Since there is no ventricular event, the operation immediately switches to the DDI/R mode. In the presence of an AT or AF, the V-V interval may time out so that paced R-wave will occur at the faster of the programmed lower rate or sensor-indicated rate in the DDI/R mode. The operation depicted in FIG. 7 may continue so long as the AT or AF persists. Upon termination of the AT, the preferred AAI/R may resume as shown in FIG. 3 or 6, depending on how the heart recovers from the AT. If the AT terminates abruptly, the prompt restoration of the atrial based pacing mode may take place (see FIG. 3). If, however, the AT "cools down" slowly, there may be a period of DDD/R pacing with periodic attempts to restore atrial based pacing as shown in FIG. 6.

Figure 8:
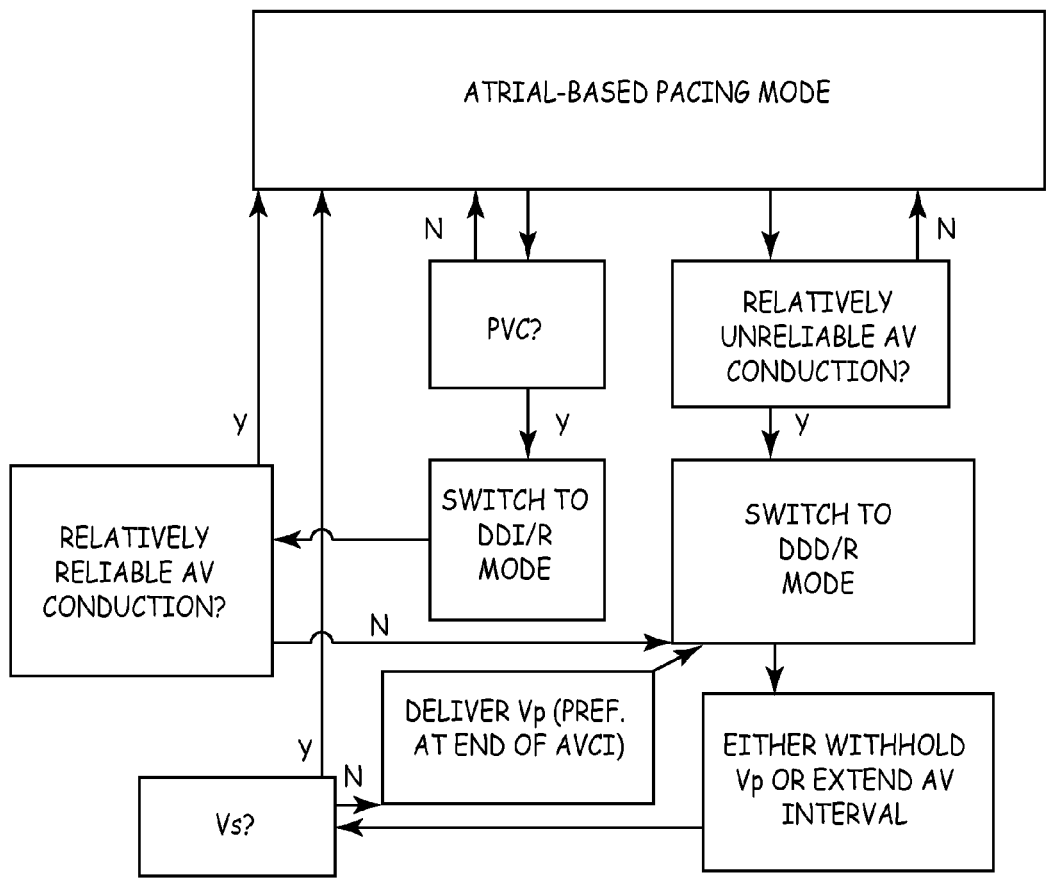
FIG. 8 is a flow chart illustrating a mode supervisor in accordance with an embodiment of the invention.

An exemplary embodiment of a mode supervisor useful for switching between an atrial based pacing mode and a dual chamber based pacing mode is generally shown in FIG. 8. In some embodiments, the mode supervisor controls a wide range of operations related to mode changes. The mode supervisor may monitor a patient's atrioventricular status and intervene when necessary by invoking sustained mode-switches to dual chamber pacing modes. According to some embodiments, the mode supervisor defines unreliable AV conduction according to a Wenckebach pattern with definition of a critical AV conduction acceptance ratio to discriminate between tolerable (or "relatively reliable") AV conduction states from intolerable (or "relatively unreliable") AV conduction states. For example, an AV conduction acceptance ratio of 4:3 allows the preferred atrial based pacing mode operation to persist as long as there are at least three ventricular events for every four physiologic atrial events. Should AV conduction falter such that the ratio of A to V events falls below the pre-defined acceptance ratio, a sustained switch to dual chamber pacing will occur. Atrial events classified as non-physiologic may not be accounted for in the calculation of the A:V ratio. Thereby, inappropriate mode-switches to dual chamber pacing are avoided in the presence of frequent non-conducted premature atrial contractions (PAC).

Upon invoking dual chamber pacing in the presence of unreliable AV conduction, the mode supervisor may immediately attempt to restore the atrial based pacing mode. Since it is known that AV conduction disease typically progresses gradually with brief manifestations of high degree block expected in the early stages of disease progression, the mode supervisor will attempt to restore atrial based pacing following only a brief episode of new onset dual chamber pacing. According to an embodiment of the present invention, the first reattempt to reveal intact AV conduction and to restore atrial based pacing will occur only after a short period of time (e.g., one minute) of dual chamber pacing. Should atrial based pacing restoration fail, reattempts will be attempted at intervals such as, for example, 2, 4, 8, 16 and 32 minutes and subsequently, for example, at 1, 2, 4, 8, 12 and 24 hours. Of course, other timing sequences may be used, both periodic and aperiodic (as well as local and remote clinician- or patient-activated atrial-based pacing initiation).

The algorithm used to search for intact AV conduction and restore ADI/R may be any algorithm useful for detecting such conduction. For example, the device may withhold a ventricular pace stimulation during dual chamber pacing operation. In the event that a ventricular sense follows the physiologic atrial event during which ventricular pacing was withheld, atrial based pacing is resumed. Otherwise, dual chamber pacing continues with subsequent reattempts according to a schedule or by way of manual activation (as specified above). As another example, the device searches for intact AV conduction involves extending the AV delay during dual chamber pacing to a pre-designated AV conduction search interval (AVCI). For instance, with an AVCI of 400 ms, the AV delay is extended to 400 ms following a physiologic atrial event (sensed or paced). In the event that the AV interval is interrupted by a ventricular sense, thereby preempting the ventricular pace in dual chamber operation, the mode supervisor reverts to atrial based pacing. Otherwise, a ventricular pace is delivered upon the expiration of the AVCI interval and dual chamber pacing operation resumes with reattempts according to the schedule (or with manual activation) as described above. In the event of failed conduction and ventricular pacing during these AV conduction search methods, an extended post-ventricular atrial refractory period (PVARP) may be invoked following the AVCI in order to guard against the possibility of retrograde conduction initiating a pacemaker mediated tachycardia.

The device 10 is also adapted to provide atrial capture management (ACM). Ensuring capture of the atrium is particularly useful in a device as described above because the atrium may be the primary chamber that is paced. Generally, two different tests may be implemented to determine atrial capture; atrial chamber reset (ACR) tests and atrioventricular conduction (AVC) tests. ACR is complementary to the AVC method in that patients do not usually have both sick sinus and AV block. During an ACR and AVC threshold test, a sequential search may be used to calculate the point at which capture is lost or gained. In some embodiments, capture and loss of capture is assessed at the same pacing value in two of three successive test paces to increase the accuracy of capture detection method by eliminating single case errors that could potentially occur due to random change in the patient's rhythm.

Figure 9A:
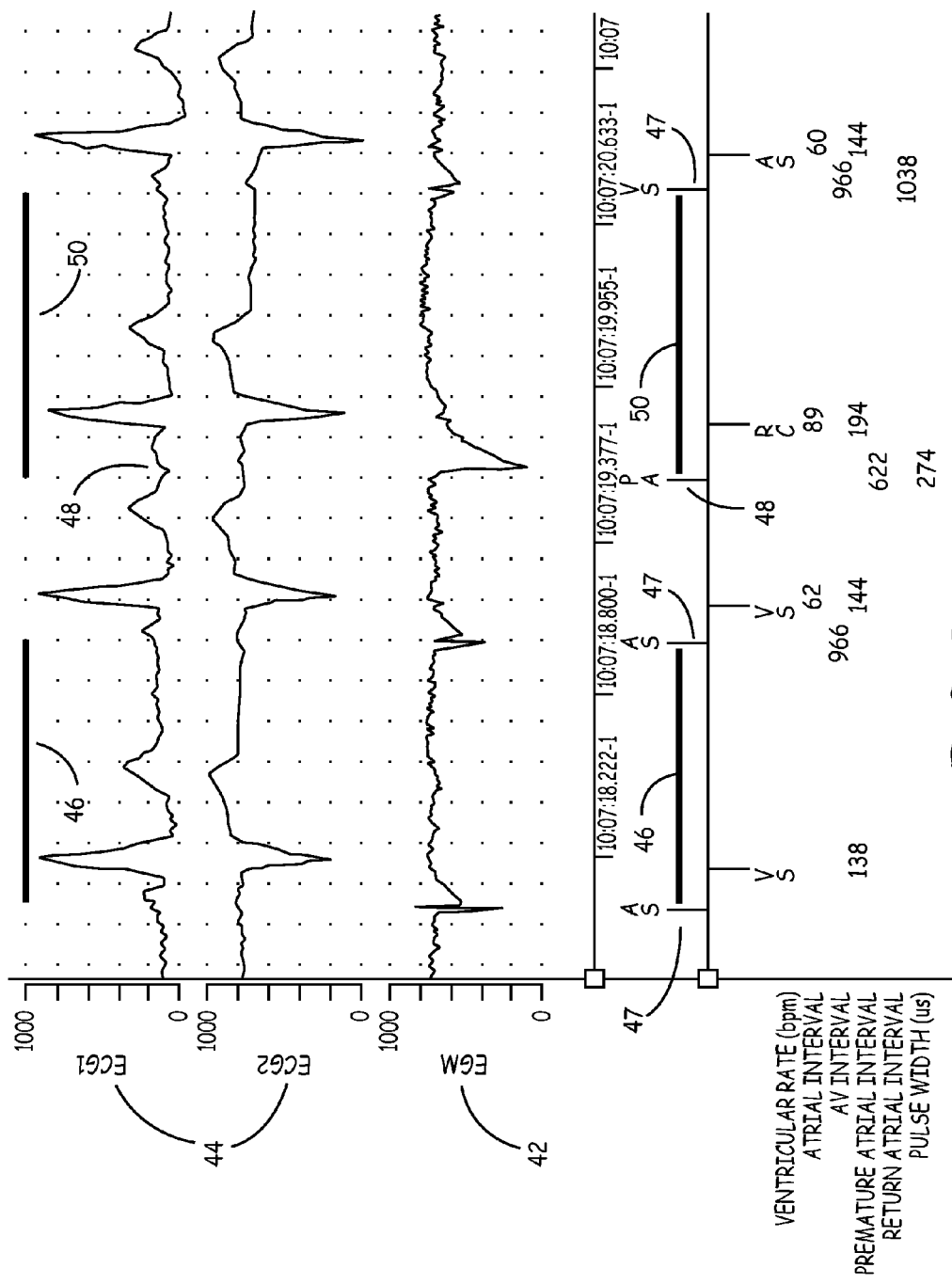
FIG. 9a is a display of ECG and EGM tracings showing capture by an Atrial Pacing Test (APt) pulse during ACR in accordance with an embodiment of the invention.

FIG. 9a is a display of ECG and EGM tracings showing capture by an APt (Atrial Pulse test pulse) pulse during ACR. EGM 42 displays atrial depolarizations that can be seen on the pacing electrode level. The difference in depolarization signals on EGM 42 is easily seen in waveforms appearing above atrial sense signals 47 and an early APt pulse 48. ECG tracings 44 are from different vectors, and typify those which are commonly found in a 12-lead ECG tracing. On ECG tracings 44, two intervals are shown. Interval 46 is the reference atrial interval before APt pulse 48, whereas interval 50 is the "return" atrial interval that occurs after the premature APt pulse 48.

During ACR, a relatively stable sinus-driven rhythm is present. ACR is intended for use with those patients who have a "stable" sinus rhythm. That is, before ACR is performed a series of stable cycles should be detected. More specifically, these AS-AS cycles are represented as interval 46 in FIGS. 9A-10. In practice, a number of these cycles should be observed before proceeding with ACR. For example, 3-10 consecutive stable cycles will generally indicate overall stability and allow for the APt pulse 48 to be initiated. In ACR, if APt pulse 48 is subthreshold, the subsequent AS 47 occurs at the previous, stable interval (see FIG. 9*b*). If APt pulse 48 is above the threshold, then it captures and resets the sinus and there is no AS at the normal interval.

A-A interval 46 represents the last in a series of stable atrial rhythm intervals. In the example shown, A-A intervals 46 at 955 ms and 50 at 1038 ms have approximately the same duration. After capture by an APt pulse 48, the return A-A interval 50 is usually a little longer than the reference A-A interval 46. This is due to the time it takes for the atrial depolarization wave (typically initiated by the atrial electrode lodged in the atrial appendage) to travel to and reset the SA node, plus the time for the next sinus-initiated wave to travel from the SA node to the atrial electrode. During the previous several seconds, the sequential sweep operation had increased the output of APt pulse until it captures the atrium at 48. At this time, the stable atrial rhythm is also interrupted only to resume again at end of interval 50. This interruption by an early APt pulse, followed by resumption of the previous stable rhythm at or close to the previous rate, determines the magnitude of the atrial output pulse required to capture the atrium.

Figure 9B:
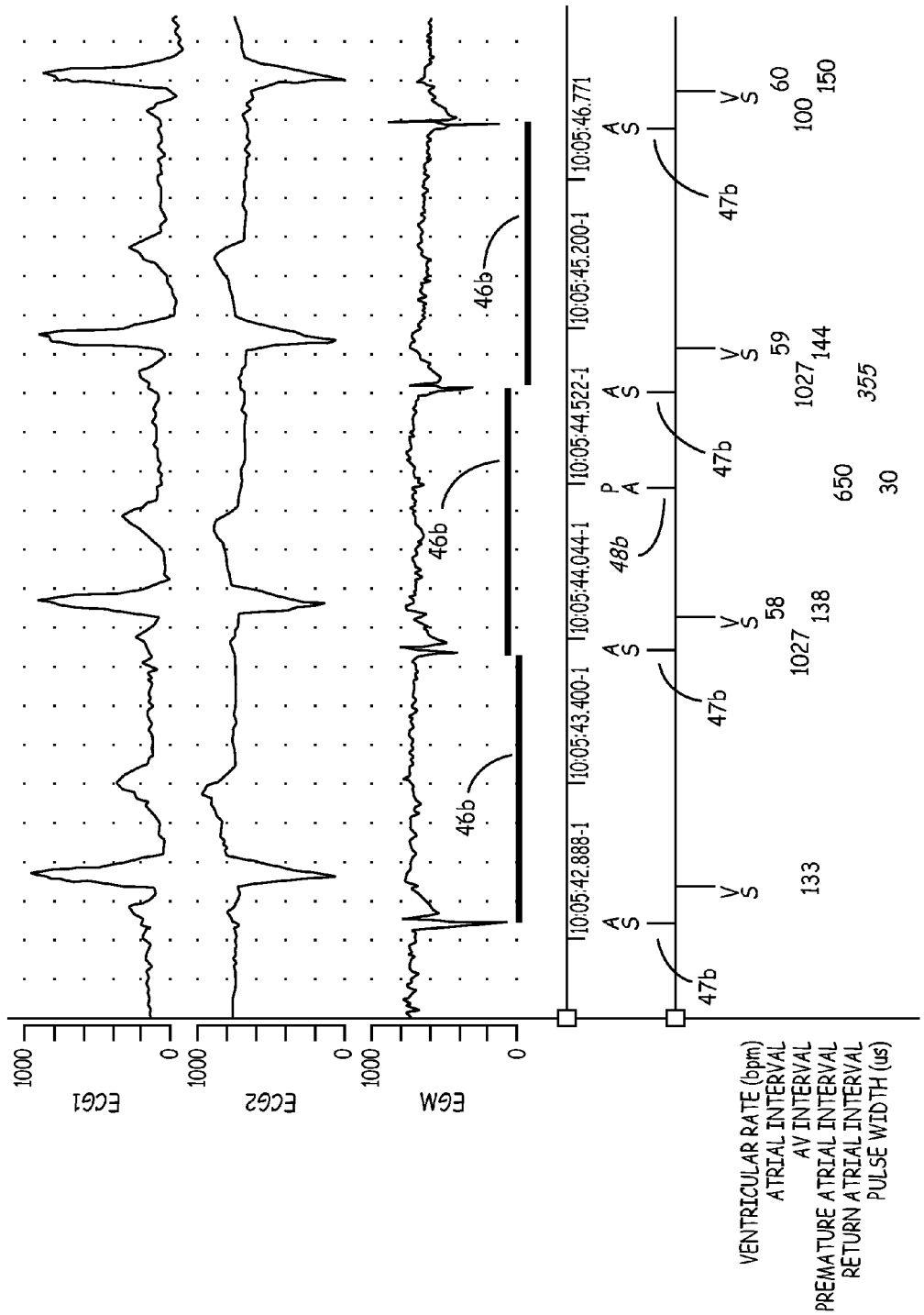
FIG. 9b is a display of ECG and EGM tracing showing LOC by an APt pulse during ACR in accordance with an embodiment of the invention.

FIG. 9*b* is a display of ECG and EGM tracing showing Loss of Capture (LOC) by an APt pulse 48*b* during ACR. As in FIG. 9*a*, Intervals 46*b* represent a stable atrial rhythm. In the example shown, A-A intervals 46*b* have approximately the same duration (1027, 1027, and 1000 ms respectively). APt pulse 48*b*, however, fails to capture the atrium. Therefore, the stable atrial rhythm continues without interruption. The algorithm recognizes the lack of interruption in the stable rhythm and "instructs" the sequential sweep to increase the atrial output for the subsequent test sequence.

FIG. 10 is a timing diagram illustrating the various intervals that correspond to FIGS. 9*a* and 9*b*. Interval 46 corresponds to an atrial reference interval, that is, one that begins with and ends with an atrial sense. APt pulse 48 occurs at interval 49 and may or may not capture the atrium, depending on its magnitude. In some embodiments, two of three such consecutive test cycles with APt pulses of the same magnitude must capture the atrium to satisfy the algorithm that a stable atrial capture has occurred.

AS (expected) 52 will occur at the prevailing sinus rate (for example, 60 bpm) if the atrium is not captured and reset by APt pulse 48. The interval from APt pulse 48 to the AS (expected) will be short, that is the time of (interval 58+interval 54). If on the other hand, the interval from the APt pulse 48 to next atrial sense is longer, that is, the time of from APt 48 to the AS 47 at the end of FIG. 10 (Interval 50), capture of the atrium by APt pulse 48 has clearly occurred.

In addition to the above, the algorithm may also take into account the normal physiologic variation in a patient's sinus rhythm. To accommodate this variation, interval 54 starts 10 bpm faster than the previous AS-AS interval, which in this example could be 60 minus 70 bpm (or 1000 minus 857 ms). Interval 54 may also be described as a "negative" sensing interval, and is generally not less than some physiologic tolerance (e.g., about 50 ms). Interval 56, on the other hand, may be described as a "positive" sensing interval and is generally of the same duration as the "negative" interval. Intervals 54 and 56, taken together, can be termed a "LOC detection window." Atrial events sensed in the LOC detection window mean that the atrial test pace did not capture the atrium. As a result, if an AS (expected) event 52 occurs in the LOC detection window (and 2-of-3 rules were met), the atrial pulse output will be increased on the next sequential sweep. Interval 58 is a blanking interval following an atrial pace during which the atrial sense amplifier is unable to sense any electrical activity in the atrium. Interval 50, started by APt pulse 48, corresponds roughly in duration to interval 46, signifying atrial capture that reset the atrium (with perhaps some lengthening due to intra-atrial conduction delay times corresponding to time required for the pacing pulse emitted from the atrial lead to travel to the sinus node and for the subsequent atrial sense originating from the sinus node to the atrial lead). Thereafter, the cycle will start again. The stability of the atrial rhythm must again be established before another APt pulse 48 is delivered or ACR is terminated when at least two of three test paces have captured. In some embodiments, once at least two of three test paces have captured the atrium and a threshold has been determined, a safety margin can be calculated and put into effect.

Figure 11:
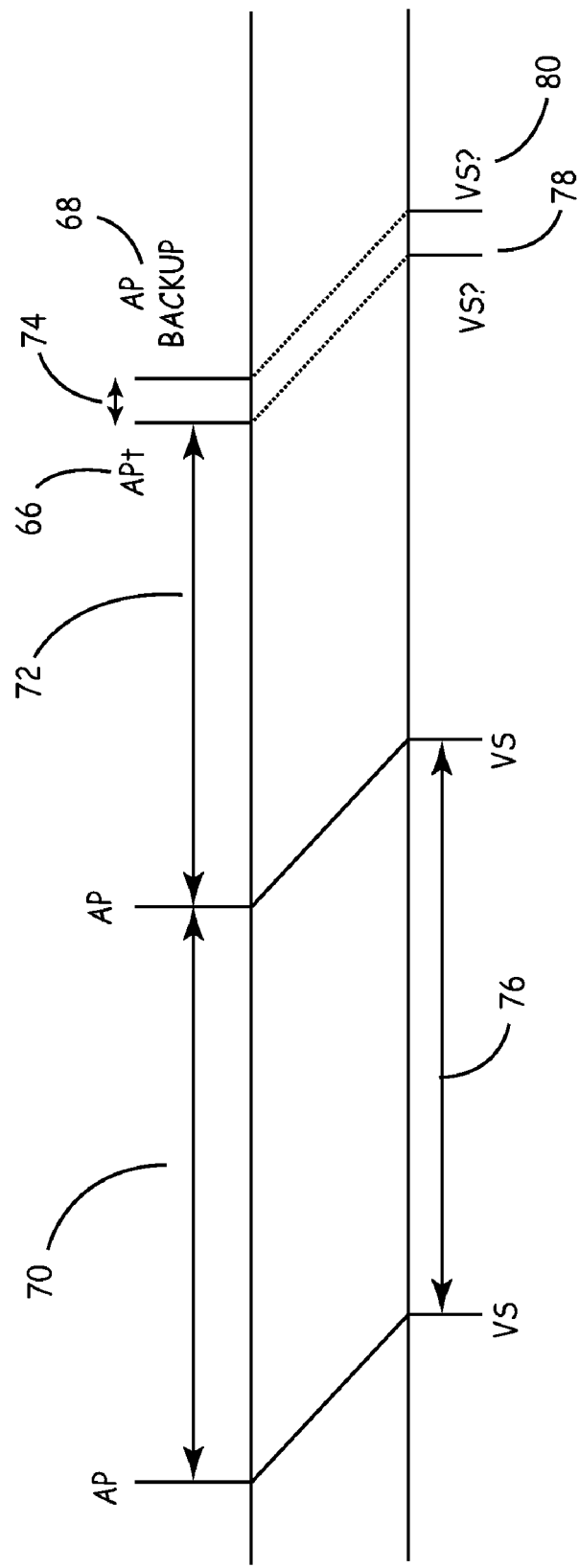
FIG. 11 is a general timing diagram that describes the AVC operation in accordance with an embodiment of the invention.

FIG. 11 is a general timing diagram that describes an embodiment of an AVC operation. In AVC, normally there is a stable atrial pace-ventricular sense (AP-VS) rhythm. A subthreshold atrial test pace will not capture the atrium and, as a result, the AP-VS rhythm is interrupted. If the test pace is above the atrial threshold, it will capture the atrium, resulting in earlier AV conduction and VS that is at 78 rather than at 80. Early conduction is the marker for capture in AVC. AVC is intended for those patients who have good AV conduction. Typically, these patients receive pacemakers for Sinus Node Disease (SND), or Sick Sinus Syndrome (SSS), among others. In some embodiments, CRT therapy may be temporarily suspended and/or the programmed AV intervals temporarily extended to run the AVC method. Further, an algorithm such as, for example, ventricular sense response (VSR) may be used to trigger a ventricular pace after the ventricle is sensed, if desired.

Further referring to FIG. 11, interval 70 is the programmed AP-AP interval that, along with interval 76, demonstrates a stable AP-VS rhythm seen at times other than the AVC operation. Interval 72 begins with an AP at the programmed/calculated output setting but terminates early in APt pulse 66. In AVC, the sequential sweep can start with the greatest magnitude (ones that maintain capture) and decrement to those with the lower magnitude (ones that lose capture), atrial threshold search methods that start with low atrial outputs (that lose capture) and increment outputs until capture is restored are possible, but measurements below and above threshold are required to determine the threshold. AVC also times APt pulses 66 to be slightly premature and highly likely to maintain capture and then slowly reduces the magnitude of these test pulses so as to eventually lose capture. Interval 74 marks the measure of prematurity and terminates with atrial backup pacing pulse 68. The prematurity interval 74 will typically range between 50 to 100 ms. Backup pulse 68 does, in fact, occur at the overdrive AP-AP interval. If VS 78 occurs, the software/algorithm determines that APt pulse 66 has captured the atrium and further energy reduction of APt pulse 66 is required to lose atrial capture. Such further reduction in pulse magnitude occurs until a VS event occurs at 80, that is, the AP-VS time previously observed during stable rhythm. When this occurs, the algorithm determines that APt pulse 66 has lost capture. If loss of capture takes place in at least two of three consecutive complexes, the algorithm goes back to the last capturing output setting and uses this setting to calculate the safety margin.

Figure 12:
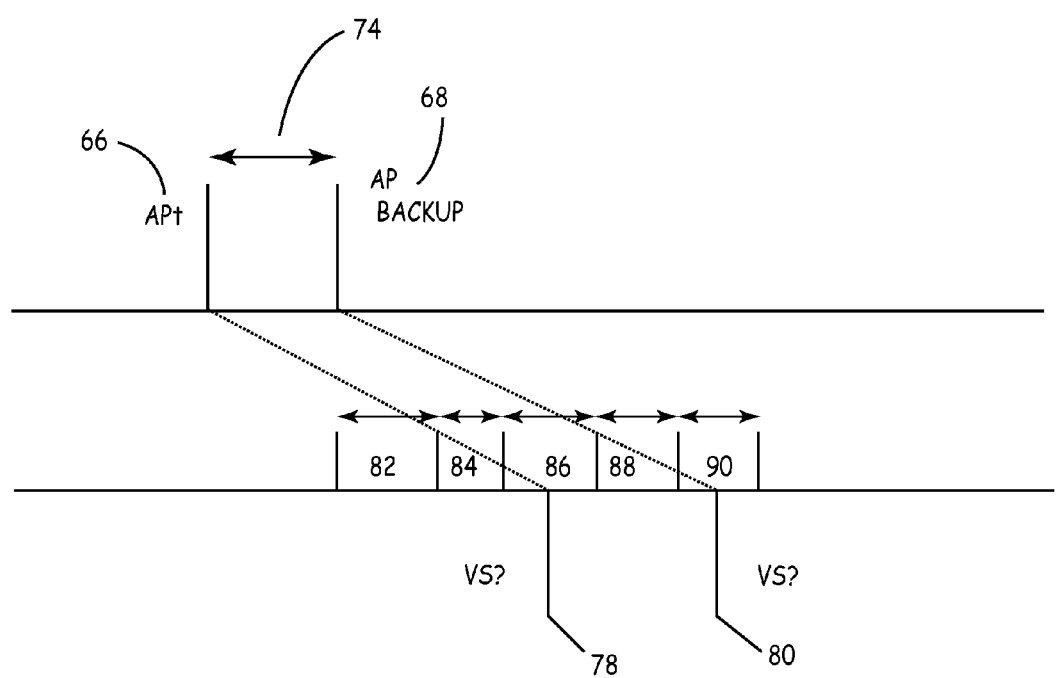
FIG. 12 is a detailed diagram of the AVC operation when an APt pulse captures the atrium in accordance with an embodiment of the invention.

FIG. 12 is a detailed diagram of the AVC operation when APt pulse 66 captures the atrium. APt pulse 66 is emitted and starts prematurity interval 74 leading to the emission of the scheduled atrial pacing pulse, here termed AP Backup 68. One of the purposes of AP backup 68 is to ensure capture when APt pulse 66 loses capture. There is no requirement that the patient be at rest for either operation to be successful. As in the case of ACR, the AVC operation may periodically emit a control pace (at output above the threshold) in the place of APt pulse 66 does not illicit a phenomenon AV conduction extension seen during increased atrial pacing and create a false negative ventricular sense at VS 80. If a VS 78 occurs on a control pace, AV conduction extension is not occurring, while a VS 80 occurrence on a control pace indicates AV conduction extension due to the slight prematurity of the control pace. The control pace is meant to eliminate a false negative, that is, one leading to the conclusion that APt pulse 66 actually lost atrial capture due to lack of conduction to the ventricle.

Interval 82 is the period during which the ventricular sense amplifier is blanked after Atrial backup pace 68. This is a function of the ventricular circuitry. Any ventricular event occurring during interval 84 is most likely due to cross talk. Any ventricular event occurring during interval 84 is ignored.

Interval 86 is the ventricular sensing window during which the algorithm looks for a sensed ventricular event. The algorithm assumes that any such sensed event during interval 86 is due to APt pulse 66. Further, any such ventricular sensed event would mean that the atrium had been captured and that the depolarization wave continues, from there, to the AV node and on to the ventricles. The duration of interval 86 is based on previous AP-VS intervals prior to the AVC operation. Interval 86 should be short enough to be specific in order to allow sensing of only those conducted events initiated by APt pulse 66. Further, interval 86 should be long enough to accommodate the normal variations in conduction time that occur. Interval 88 represents a variation in conduction from either APt pulse 66 or AP backup pulse 68. Interval 88 is wide enough so that any VS event occurring therein must be discounted. A VS within interval 88 will be ignored for purposes of capture and will constitute an abort criteria for potentially aborting the threshold search if a number of VS intervals are detected in interval 88. Because the AVC operation requires at least two of three ALOC events, an individual VS event within interval 88 would be ignored during AVC operation, whereas continued ventricular sensing in interval 88 would abort the AVC operation.

A VS event occurring in interval 90 means that the atrium was captured by AP backup pulse 68 and that APt pulse 66 failed to capture the atrium. Thus, interval 90 is referred to as the LOC window. In practice, the LOC window 90 will be set between approximately 5-100 ms in duration. Such ALOC either counts toward fulfillment of the two of three criteria, or fulfills that criterion. In the latter case, the algorithm uses the previous pulse magnitude that captured the atrium as a basis for calculating the appropriate safety margin. Generally, after delivery of the APt 66 and the delivery of the AP backup 68 there should be a VS in either the ventricular sensing window 86 or the LOC window 90, dependent upon whether the first or second pulse captures.

When evaluating the timing for the prematurity window 74, the ventricular sensing window 86, and the LOC window 90, the granularity of the time base of the hardware must be considered. That is, any given window will simply be a multiple of the clock pulses utilized for timing, which is device dependant. As a further consideration, there should be a correspondence between the prematurity window 74 and the LOC window 90. In one embodiment, the duration of the LOC window 90 is less than or equal to the duration of the prematurity window 74. In this manner, a VS can accurately be determined to have originated from the APt 66 or the backup pace 68 that was initiated after the duration of the prematurity window 74.

As described above, pacing in the ventricle may be discouraged by biasing the device 10 to pace in an atrial based pacing mode. Ensuring capture of the atrium is particularly useful in such a device as the atrium may be the primary chamber that is paced. Some embodiments of the invention include an implantable medical device having means for selecting between an ACR test and an AVC test and means for switching between an atrial-based pacing mode and a dual chamber pacing mode based on detecting relatively reliable atrioventricular conduction. In some embodiments, the means for selecting between the ACR and AVC tests may select the ACR test when the device is in the dual chamber mode. Further, the means for selecting between the ACR and AVC tests may select the AVC test when the device is in the atrial-based pacing mode. Alternatively, the device may also choose the ACR test when the device is in the atrial-based pacing mode. Generally, the means for selecting and means for switching may be any circuit and/or algorithm suitable for this purpose. Further, the invention also includes a software system adapted to provide ACM in MVP modes.

Figure 13:
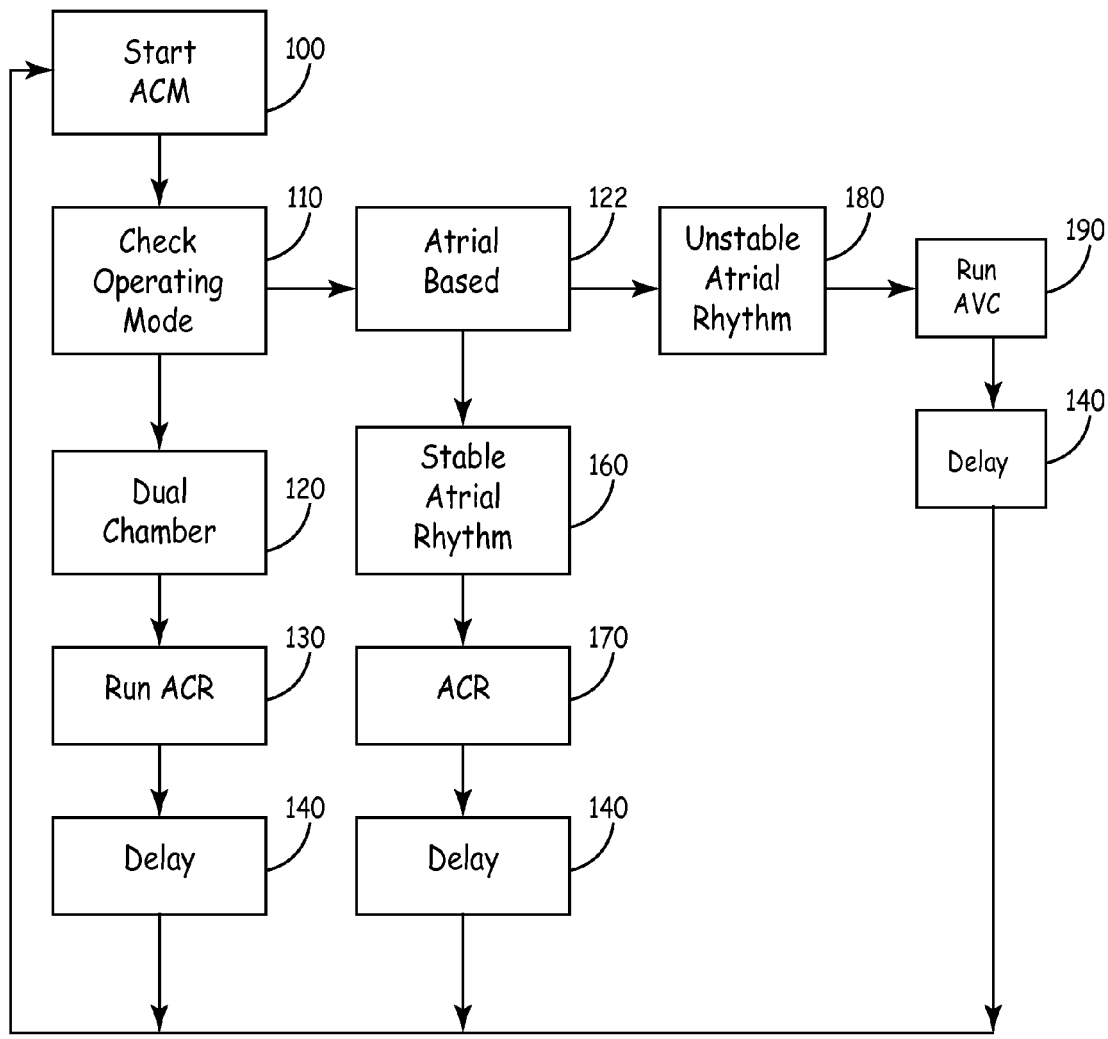
FIG. 13 is a flow diagram illustrating the implementation of ACM in a device provided with MVP in accordance with an embodiment of the invention.

With reference to the embodiment shown in FIG. 13, the device 10 may start ACM testing protocol 100 at a programmed period of time, such as "daily search," "daily fixed," or a period of time less than or greater than a 24-hour daily schedule. Upon activation of the ACM testing protocol 100, the device 10 checks its present operating mode 110 to determine if it is operating in a dual chamber pacing mode 120 or an atrial based pacing mode 122 according to the MVP algorithm described above. If the device 10 is operating in a dual chamber pacing mode 120, it will attempt to run the ACR test method 130. The AVC test method is not considered because a lack of relatively reliable AV conduction has already been determined as the device 10 is operating in a dual chamber pacing mode. Either upon a successful ACR test or an aborted ACR test, a delay 140 will occur before the ACM test protocol 100 is reattempted.

If the device 10 determines it is operating in the atrial based pacing mode 122 after checking the operating mode 110, the device 10 may run either the ACR test or the AVC test. In some embodiments, the device 10 will run the ACR test 170 when the patient is showing a stable atrial rhythm 160. In such embodiments, the device may confirm an appropriate rhythm and not proceed with an ACR test unless a stable rhythm has been established.

While the device 10 is in an atrial based pacing mode the AVC test may also be attempted because relatively reliable AV conduction has previously been determined. In some embodiments, the device 10 may run AVC test 190 when the patient has a relatively unstable atrial rhythm 180. Regardless of whether AVC test 190 or ACR test 170 is run, or whether the tests were successful or ended in an abort, a delay 140 may be set before the ACM testing protocol 100 is reattempted.

Other methods may be used to choose whether AVC test 190 or ACR test 170 is attempted while the device 10 is in an atrial based pacing mode. For example, if atrial pacing and ventricular sensing is occurring the AVC method may be selected. Alternatively, if atrial sensing is found, then the ACR method may be selected. As another example, choosing between ACR 170 and AVC 190 when the device 10 is in the atrial based pacing mode 122 may also be linked to the success of previous ACM attempts or based on other programmed criteria. For example, after successfully achieving one method, a bias can be flagged to select the same method for subsequent tests. Also, a limit may be placed on the number of each of the AVC or ACR protocols that may be attempted per a unit time (e.g., 3 attempts per day). If such a limited is utilized, the flag can be used to bias towards an untried protocol. For example, if AVC has been attempted several times without success, the flag can bet set to favor ACR at the next attempt.

In some embodiments the MVP mode may retain atrial based pacing when AV conduction times exceed about 400 ms. In such embodiments, the AVC method may be attempted under such circumstances. In contrast, many traditional dual chamber pacing devices would not tolerate an AV conduction time of that length without pacing the ventricle. Therefore, allowing the AVC method to run in an atrial based pacing mode of MVP may reduce AVC test aborts due to long AV conduction times relative to traditional dual chamber devices and/or allow the atrial threshold to be measured in patients who exhibit prolonged AV conduction. Further, the potential for pace-on-T scenarios during AVC is reduced relative to traditional dual chamber devices because the ventricle is not paced with the device is operating in the atrial based pacing mode.

In general, ACM is performed on a periodic basis, e.g., once per day, in order to determine an appropriate threshold level, as previously indicated. In order to properly determine the threshold level a certain degree of stability should be observed prior to initiating any test pulse and when determining if capture occurs. In order to assure higher accuracy in measurement and prevent the ACM protocol from cycling and possibly generating patient symptoms, an abort counter step (not shown) may be utilized. The abort counter keeps a running count of certain triggering events and if a predetermined level of such events is reached, the ACM test protocol is aborted. Examples of such events include PVC's, PAC's, Ventricular Refractory Senses, Atrial Refractory Senses, AS-AS interval variability, and AP-VS interval variability. If instability or a condition is detected, the abort counter is incremented by a value. In some embodiments, the value is weighted based on severity as determined by a predetermined value for each instability or a given condition.

In general, when the abort counter exceeds a predetermined value, the system may be prevented from reinitiating the ACM testing protocol for some predetermined period of time, e.g., 30 minutes. In addition, there may also be a daily limit to the number of attempts allowed, e.g., three. Thus, if unexpected conditions are encountered or the requisite stability is absent, the ACM test protocol can abort without determining a threshold value and if such conditions persist, may not find a threshold over the course of the entire day. In some embodiments, the invention reduces the number of ACM test aborts because the AVC test is not attempted in the device is operating in the dual chamber pacing mode, where lack of relatively reliable AV conduction has previously been determined.

Figure 14:
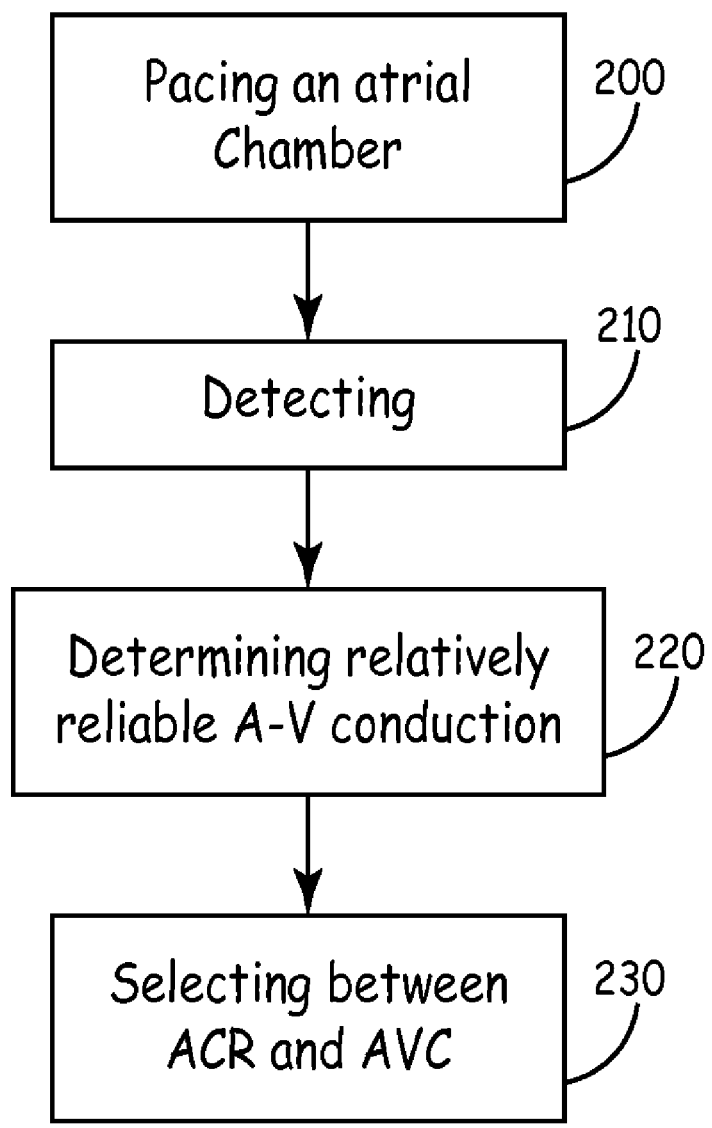
FIG. 14 is a flow diagram illustrating a method of providing ACM in a device provided with MVP in accordance with an embodiment of the invention.

The invention also includes a method of providing capture management to an implantable medical device biased towards an atrial-based pacing mode. The steps of a method in accordance with an embodiment of the invention is shown in FIG. 14, which generally shows the steps of pacing an atrial chamber 200, detecting 210, determining relatively reliable A-V conduction 220, and selecting between ACR and AVC 230 as described herein. In some embodiments, the method includes pacing an atrial chamber of a heart pursuant to the atrial-based pacing mode, detecting an intrinsic ventricular depolarization, determining whether a relatively reliable atrioventricular conduction condition exists, and if the conduction condition is present continuing the atrial-based pacing mode, and if the conduction condition is not present mode switching to a dual chamber pacing mode; and selecting between an atrial chamber reset (ACR) test and an atrioventricular conduction (AVC) test to provide atrial capture management, wherein the ACR test is selected when the medical device is in the dual chamber pacing mode. In some embodiments, the invention includes a computer-readable medium comprising instructions for performing the various methods described herein.

One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device comprising:
    means for determining whether the device is operating in a dual chamber pacing mode or in an atrial-based pacing mode;
    means for selecting an atrial chamber reset (ACR) test in response to the device operating in the dual chamber pacing mode; and
    means for selecting either of the ACR test and an atrioventricular conduction (AVC) test in response to the device operating in the atrial-based pacing mode.

2. A device according to claim 1, wherein the means for selecting either of the ACR test and the AVC test selects the AVC test when unstable atrial pacing is occurring.

3. A device according to claim 1, wherein the means for selecting either of the ACR test and the AVC test selects the AVC test when unstable atrial pacing is occurring and a patient atrioventricular conduction time exceeds 400 ms.

4. A device according to claim 1, wherein the means for selecting either of the ACR test and the AVC test selects the ACR test when stable atrial sensing is occurring.

5. A device according to claim 1, wherein the atrial-based pacing mode is selected from the group of ADIIR and AAIIR pacing modes.

6. A device according to claim 1, wherein the dual chamber pacing mode is selected from the group of DDDIR and DDIIR pacing modes.

7. A software system implemented in a medical device system comprising:
    a control circuit programmed to select an atrial chamber reset (ACR) test in response to the medical device system operating in a dual chamber pacing mode and to select between the ACR test and an atrioventricular conduction (AVC) test in response to the medical device system operating in an atrial-based pacing mode.

8. A system according to claim 7, wherein the AVC test is selected when unstable atrial sensing is occurring.

9. A system according to claim 7, wherein the ACR test is selected when the implantable medical device is in the atrial-based pacing mode and stable atrial sensing is occurring.

10. A system according to claim 7, wherein the atrial-based pacing mode is selected from the group of ADIIR and AAIIR pacing modes.

11. A system according to claim 7, wherein the dual chamber pacing mode is selected from the group of DDDIR and DDIIR pacing modes.

12. A method of providing capture management to an implantable medical device biased towards an atrial-based pacing mode, comprising the steps of:
- determining whether the medical device is operating in a dual chamber pacing mode or in an atrial-based pacing mode;
- selecting an atrial chamber reset (ACR) test in response to the medical device operating in the dual chamber pacing mode; and
- selecting between the ACR test and an atrioventricular conduction (AVC) test in response to the medical device operating in the atrial-based pacing mode.

13. A method according to claim 12, wherein the AVC test is selected when the implantable medical device is in the atrial-based pacing mode and unstable atrial pacing occurring.

14. A method according to claim 12, wherein the AVC test is selected when the implantable medical device is in the atrial-based pacing mode, unstable atrial sensing is occurring, and a patient atrioventricular conduction time exceeds 400 ms.

15. A method according to claim 12, wherein the ACR test is selected when the implantable medical device is in the atrial-based pacing mode and stable atrial pacing is occurring.

16. A method according to claim 12, wherein the atrial-based pacing mode is selected from the group of ADIIR and AAIIR pacing modes.

17. A method according to claim 12, wherein the dual chamber pacing mode is selected from the group of DDDIR and DDIIR pacing modes.

18. A non-transitory computer-readable medium having computer executable instructions for performing a method, the method comprising:
- determining whether the medical device is operating in a dual chamber pacing mode or an atrial-based pacing mode;
- selecting an atrial chamber reset (ACR) test in response to the medical device operating in the dual chamber pacing mode; and
- selecting between the ACR test and an atrioventricular conduction (AVC) test in response to the medical device operating in the atrial-based pacing mode.

* * * * *